United States Patent [19]

Adrion et al.

[11] 4,117,338
[45] Sep. 26, 1978

[54] AUTOMATIC RECORDING FLUOROMETER/DENSITOMETER

[75] Inventors: Robert F. Adrion, Big Flats, N.Y.; Robert T. Buck, Raleigh, N.C.; William R. Eppes, Painted Post, N.Y.

[73] Assignee: Corning Glass Works, Corning, N.Y.

[21] Appl. No.: 800,004

[22] Filed: May 24, 1977

[51] Int. Cl.² .......................................... G01N 21/38
[52] U.S. Cl. .............................................. 250/461 R
[58] Field of Search .................. 250/458, 459, 461 R, 250/461 B; 356/36, 39, 51, 96, 246

[56] References Cited

U.S. PATENT DOCUMENTS

| | | | |
|---|---|---|---|
| 3,800,161 | 3/1974 | Scott et al. | 250/458 X |
| 3,832,557 | 8/1974 | Bazholin et al. | 250/461 |
| 3,916,205 | 10/1975 | Kleinerman | 250/461 B |

*Primary Examiner*—Davis L. Willis

*Attorney, Agent, or Firm*—Walter S. Zebrowski; Clarence R. Patty, Jr.; Richard E. Kurtz

[57] ABSTRACT

An automatic recording fluorometer/densitometer has an integral viewer for viewing and photographing fluorescent samples which have been applied to a clear, thin-film substrate. Light from an ultraviolet source is on the opposite side of the sample from the viewer when the sample is placed in a viewer holder. When the sample is placed in a recording holder, light from the same source is on the opposite side of the sample from the recorder optics. By having the source on the opposite side from the optics, it is possible to have the source much closer to the sample and to thereby reduce the stray ultraviolet light in the instrument. Another source emits visible light for densitometric analysis of the sample. A movable filter holder can be indexed to different positions for placing an ultraviolet filter or one of the densitometric filters in the optical path between the sources and the recording device.

22 Claims, 6 Drawing Figures

AUTOMATIC RECORDING FLUOROMETER/DENSITOMETER

BACKGROUND OF THE INVENTION

This invention relates to an automatic recording fluorometer/densitometer.

Zonal electrophoresis has been successfully used in clinical laboratories. Electrophoresis is a separative procedure based on the phenomenon that electrically-charged molecules or particles will migrate through a solution or gel in response to an externally applied voltage gradient. Many biological molecules, especially proteins, carry a net electric charge in solution which makes them susceptible to electrophoretic forces.

In the zonal electrophoresis technique, a small volume of biological fluid (e.g., blood serum, cerebrospinal fluid, etc.) is applied at one spot on a buffer-saturated membrane or thin-layer medium. When a voltage difference is established across the ends of the medium, different molecular species in the sample migrate with different velocities, and with time, resolve into a series of distinct bands or spots. The desired molecular bands can be visualized by direct staining with specific dyes, or in the case of certain enzymatic samples, by applying chemical substrates that become catalytically converted to colored or fluorescent products. Deviations from normal in the intensity or mobility of the bands revealed by a given test are associated with biochemical abnormalities that may indicate a particular pathology.

Electrophoresis is often effective in separating nearly identical biomolecules, since minor differences in charge and molecular conformation may result in noticeably different electrophoretic mobilities. Similar electrophoretic procedures can be applied to a wide variety of clinical tests, since the specificity of a given test is largely determined by the dyes or reagents used in the final processing. The simplicity, rapidity and versatility of zonal electrophoresis, as well as its general effectiveness, make it an attractive basis for clinical determinations that require the separation of biomolecules.

U.S. Pat. Nos. 3,479,265 and 3,635,808 disclose thin film agarose plates which can be used as the electrophoretic medium. The thin film plates of these patents are particularly convenient for handling and storage.

Electrophoresis preparations or samples can be grouped into two categories, densitometric and fluorometric. Densitometric (sometimes called colorimetric) samples have bands that absorb visible light and are thus observable in normal room light. Fluorometric samples absorb ultraviolet light and fluoresce, emitting light at visible wavelengths. Thus fluorometric samples cannot be seen in normal room light but must be excited with ultraviolet light to be observed.

Qualitative clinical evaluation of electrophoresis samples can be done by visual inspection, i.e., gross abnormalities can be detected in this way. However, the present state-of-the-art in clinical medicine typically requires a more critical quantitative evaluation.

Quantitative evaluation of electrophoresis preparations requires the generation of an optical density profile or fluorescence intensity profile of the sample, whichever is appropriate.

The optical density profile is partitioned into individual peaks each representing a band on the electrophoretic separation. Adjacent peaks are separated by recognizing and selecting a valley. Integration of the area under each individual peak and computation of the peak area as a percentage of the total area under the profile represents, for example, the distribution of certain proteins in blood serums. Norms for such distributions have been established, and deviation from these norms is of diagnostic significance. The percentage numbers are sometimes multiplied by a "scale factor" so that the results are in units of protein concentration or enzyme activity, rather than percent of total.

One instrument for automatically making analyses of the aforementioned type is described in U.S. Pat. No. 3,706,877.

In addition to automatically recording the concentration distributions of the film, it is desirable to directly view the films. Fluorometric iso-enzyme samples have bands of iso-enzymes dispersed along the length of any given sample which cannot be seen in room light. The sample must be shielded from visible light and illuminated with ultraviolet light in order to see the iso-enzyme bands.

Currently available viewers for fluorescing samples usually make use of a hand held source of ultraviolet radiation in a darkened room or a sample is inserted into a box and viewed through a port with the sample being viewed from the same side that it is illuminated. Inherent in this arrangement is both reduced intensity and reduced uniformity since bulbs must be placed outside the field of view and relatively distant from the sample. State of the art fluorescent viewing devices do not provide operator protection from exposure to ultraviolet radiation.

SUMMARY OF THE INVENTION

In accordance with this invention, a single instrument provides a comprehensive quantitative evaluation of clinical electrophoretic samples.

In accordance with this invention, the optical density and fluorescence intensity of a sample are measured and recorded in an instrument which can be changed between the fluorometric mode of operation or the densitometric mode at different light wavelengths as appropriate to the particular sample being evaluated.

In accordance with this invention, an integral fluorometric viewer makes it possible to visually inspect fluorometric samples as a screening operation prior to further evaluation.

In accordance with a further aspect of the invention, fluorometric and densitometric light sources are on the opposite side of the sample from the recording device and the fluorometric source is located on the opposite side of the sample from the viewer. This permits the light sources to be quite close to the sample to maximize excitation of the sample, while at the same time the sources do not block the optical path between the sample and the recorder or the optical path between the sample and the viewer.

In accordance with another important aspect of the invention, good shielding of the ultraviolet light is provided. The ultraviolet light sources are located close to the sample and on either side of the optical axis so that geometric shielding of the ultraviolet light from the recording device is possible.

The integral viewer includes an ultraviolet blocking filter located in the bottom opening of the viewer in such a manner that the observer is completely shielded from ultraviolet light. Ambient light is excluded from the viewer. Because the ultraviolet source is on the opposite side of the sample, it can be positioned quite close to the sample for good excitation but the observer does not see the source because of a selective transmission filter.

The foregoing and other objects, features and advantages of the invention will be better understood from the following more detailed description and appended claims.

DESCRIPTION OF THE DRAWINGS

FIG. 3A shows the indexing mechanism for the mode selector;

DESCRIPTION OF THE PREFERRED EMBODIMENT

Figure 1:
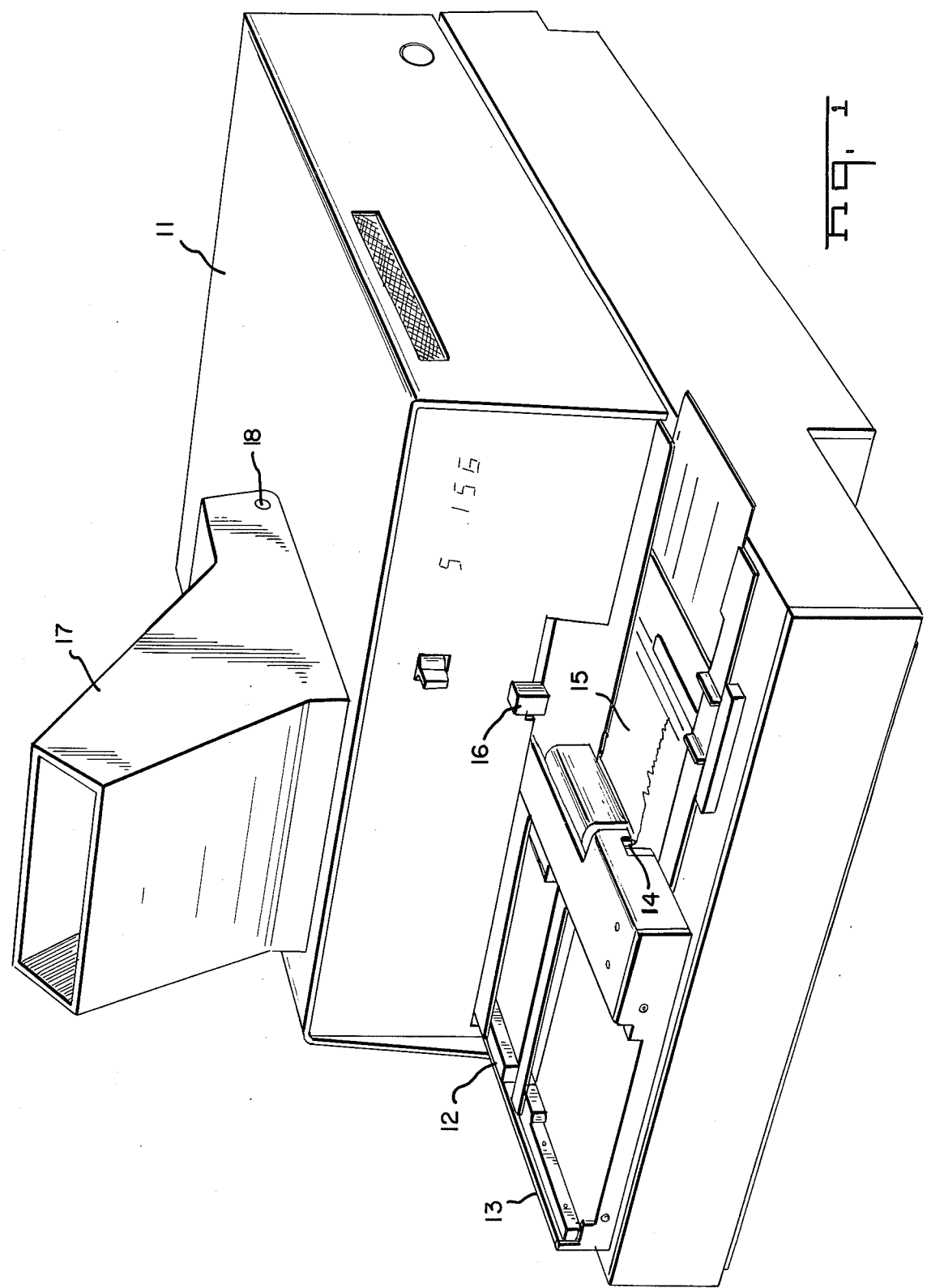
FIG. 1 is a perspective view of the instrument of this invention.

The instrument of this invention includes a case 11 which encloses the fluorometric and densitometric sources and optics. For automatic recording, the film sample is inserted in the recording sample holder 12. The sample holder slides into the case between the light sources and the optics for the recording system. The scanning stage 13 moves in a horizontal direction to scan the light across the film. Concurrently, a recording pen 14 moves across the chart 15. A light detector measures light intensity from the sample, and the recording system responds to the output of the detector to move the recording pen 14 orthogonally to the scanning motion. This records the intensity of fluorescing or densitometric light from the sample. The recording device is more fully disclosed and claimed in co-pending application Ser. No. 799,942 filed May 24, 1977, Amos et al, Recording Analyzer for Electrophoretic Sampler.

In order to select the mode of measurement, a mode selection knob 16 is provided. This knob is set to make either a fluorometric analysis or one of three densitometric analyses at wavelengths of 450, 520 and 600 nanometers.

An integral viewer includes a shroud 17. The viewer is used to visually inspect fluorometric samples as a screening operation prior to further evaluation. Shroud 17 is hinged at 18 to the instrument case 11. The shroud shields the sample from visible light so it can be illuminated with ultraviolet light in order to see the isoenzyme bands dispersed along the length of the sample. The shroud 17 is tilted on its hinge and the sample is placed in a viewing sample holder formed between the case and the shroud.

Figure 2:
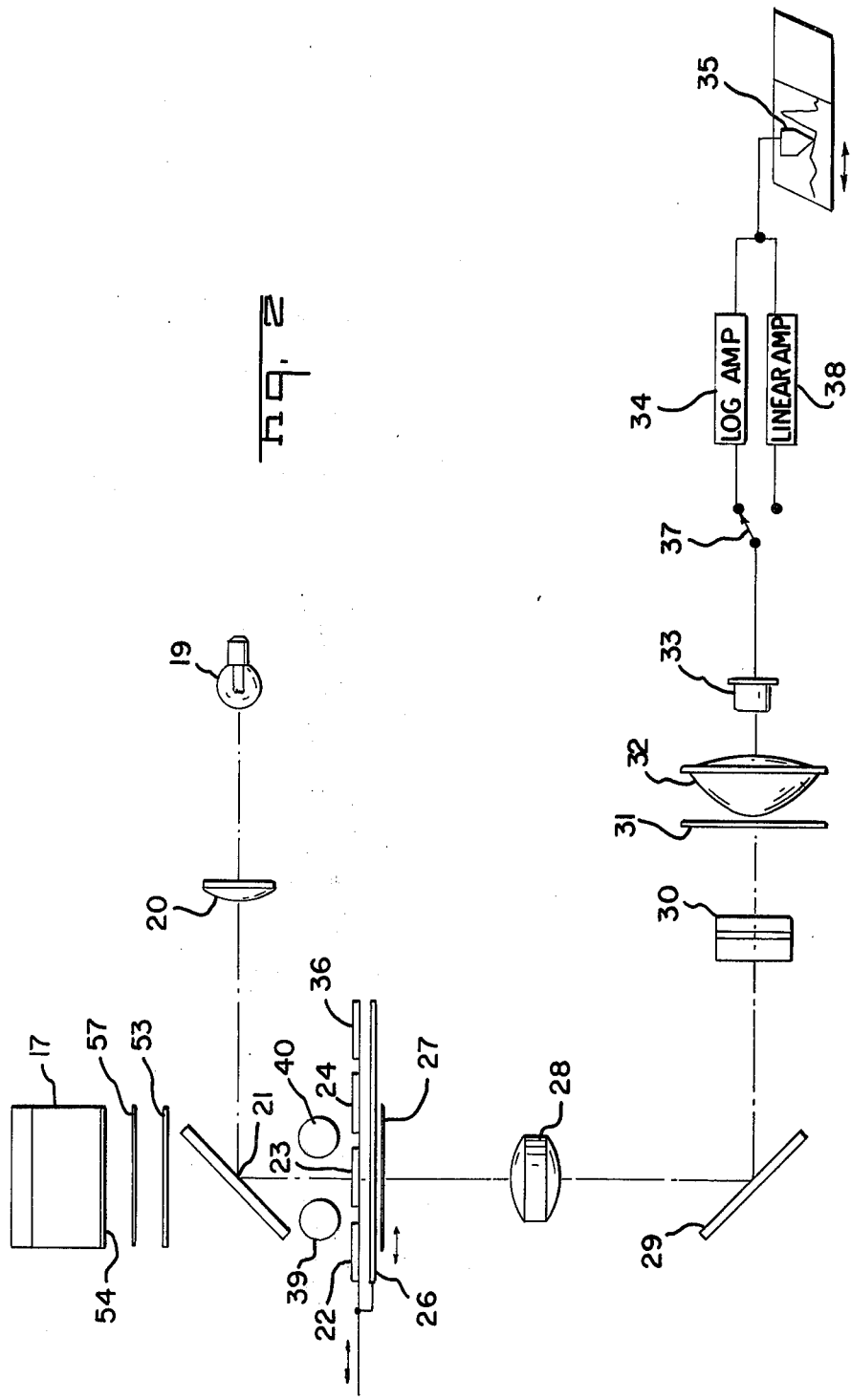
FIG. 2 is a schematic diagram of the optics.

Referring to FIG. 2, the instrument includes an incandescent lamp 19 used as a source for making densitometric measurements at different visible wavelengths. Lens 20 and fold mirror 21 direct light through one of the three densitometric filters 22, 23 or 24 mounted on the filter holder 25 (FIG. 3) which is moved to place the appropriate filter in the optical axis. An aperture stop 26 is in close proximity to the sample 27 and determines the optical resolution in densitometry.

The sample is moved from right to left during its scanning and it absorbs light in accordance with the optical density of the sample. Light passing through the sample is gathered by the objective lens 28, reflected by the mirror 29 and passes through secondary filter 30. Filter 30 is a compound filter which transmits only light of the desired band of wavelengths. Densitometric light passing through the aperture 26 is imaged on the second aperture 31 so all of the densitometry light passes through this second aperture.

An aspheric lens 32 forms an image of the objective lens exit pupil on the photo diode detector 33, so that all the light collected by the lens 32 is sensed by the detector 33. The output of detector 33 is applied to a logarithmic amplifier 34 which produces an electrical signal proportional to optical density or absorbence of the sample. This signal is applied to the recording device 35 which records absorbence.

Photo diodes are linear devices. A signal proportional to the density of the sample is equal to a constant times the logarithm of the light passing through the sample. In order to use the same detector 33 and recording device 35 for both densitometric and fluorometric measurements, it is necessary to use a logarithmic amplifier 34 in densitometric measurements.

In the fluorometric mode of operation, the filter holder 25 is moved to place the ultraviolet transmission filter 36 in the optical path. Mode switch 37 is changed to apply the output of detector 33 to a linear amplifier 38. The aperture 26 is changed from an 0.4 × 2.5 millimeter aperture to a 8 × 13.5 millimeter aperture. Another switch, not shown in FIG. 2, deenergizes the incandescent lamp 19 and energizes ultraviolet lamps 39 and 40.

Light from ultraviolet lamps 39 and 40 passes through the ultraviolet transmission filter 36 and through the aperture stop 26 to excite the sample 27. The emitted fluorescence is collected by the objective lens 28 and passes through the secondary filter 30 which blocks any stray ultraviolet light. The objective lens 28 forms an image of the excited area of the sample on the second aperture 31. This aperture determines the optical resolution of the system in the fluorometric mode. The aspheric lens 32 forms an image of the objective lens exit pupil on the photo diode detector 33, so that all the light collected by the lens 32 is sensed by the detector 33.

The ultraviolet lamps 39 and 40 are located quite close to the sample and at 45° from the optical axis. This minimizes the size of the excited area of the sample and controls stray ultraviolet excitation light. Excitation light which passes through the sample 27 is geometrically excluded from entering the objective lens 28. The system provides good geometric and spectral discrimination against excitation light. In the prior art, ultraviolet excitation lamps are on the same side of the sample as the detection optics. In such systems, it is virtually impossible to exclude ultraviolet excitation light from the detection system.

The dual imaging system including movable aperture stop 26 gives good fluorescence collection efficiency, precise control of optical resolution, and allows use of a small area solid state photo diode detector.

Figure 3:
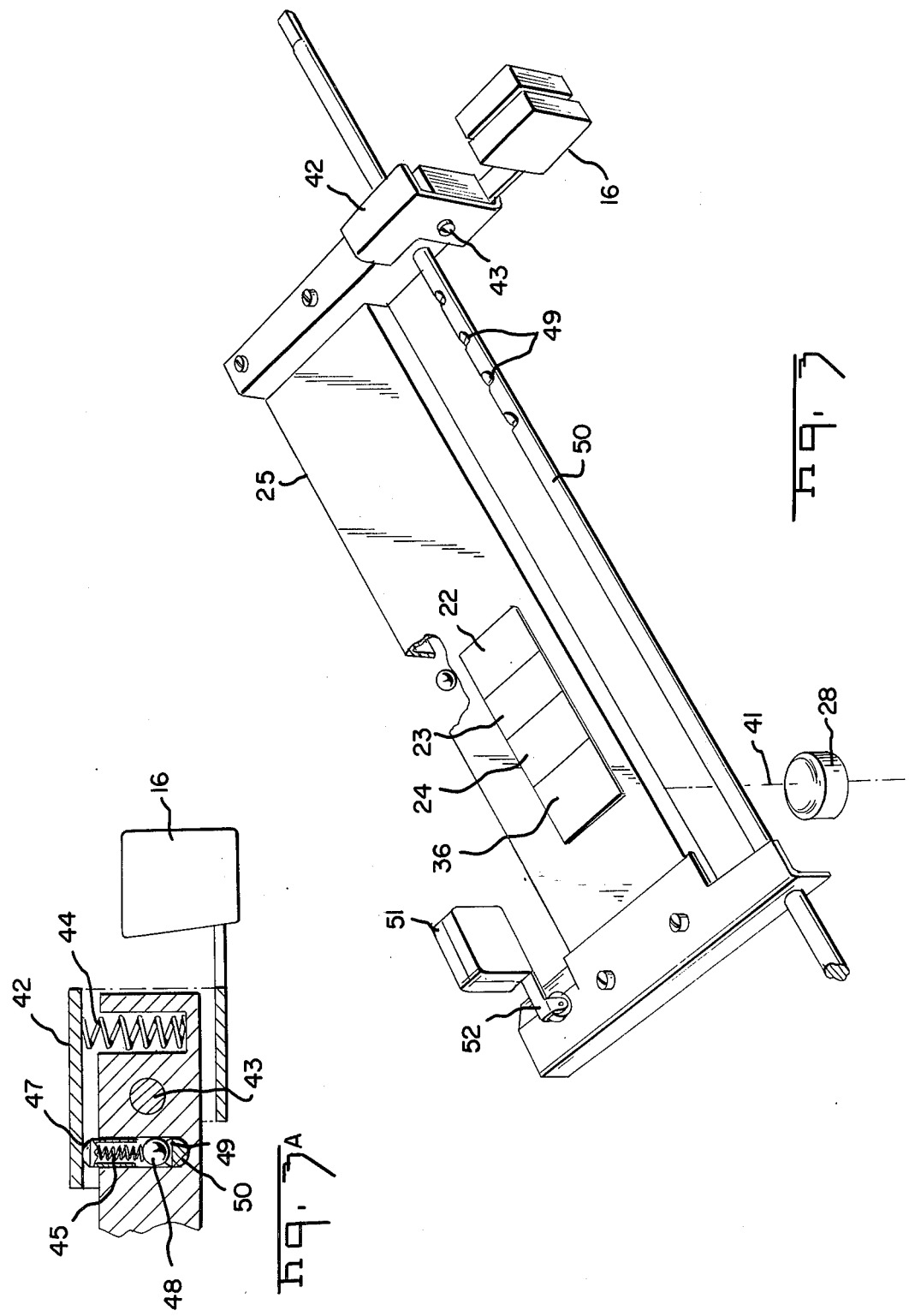
FIG. 3 shows the filter mode selector.

The mode selector is shown in FIGS. 3 and 3A. FIG. 3 shows the mode selection mechanism for indexing the various filters and their respective apertures precisely over the optical center line 41. Filters 22, 23, 24 and 36 respectively pass 600 nanometer, 520 nanometer, 450 nanometer and fluorometric light. An aperture is provided beneath each filter. The index mechanism includes knob 16 which moves lever 42 pivoted at 43.

FIG. 3A shows a cross-section through the mechanism exposing primary spring 44, secondary spring 45 and push rod 47. When the knob 16 is depressed, the bias on ball 48 is released, allowing it to be moved out of one of the detents 49 in the way rod 50. The filter holder 25 slides along way rod 50 to a new position.

The purpose of the secondary spring 45 is to maintain slight pressure on the ball 48 so that the operator has some feedback "feel" and knows when a detent is present.

Mode selection switches 51 have an actuating arm 52 which is actuated by the movement of the holder. When the optical axis passes through the fluorometric filter 36, as shown, the actuator 52 is depressed, thereby turning on the ultraviolet lamps 39 and 40 and connecting detector 33 to the linear amplifier 38 (FIG. 2).

In any position other than fluorometric, the actuator 52 of the mode switch is released, thereby turning off the ultraviolet lamps, turning on incandescent lamp 19 and connecting the detector 33 to the logarithmic amplifier 34.

Figure 4:
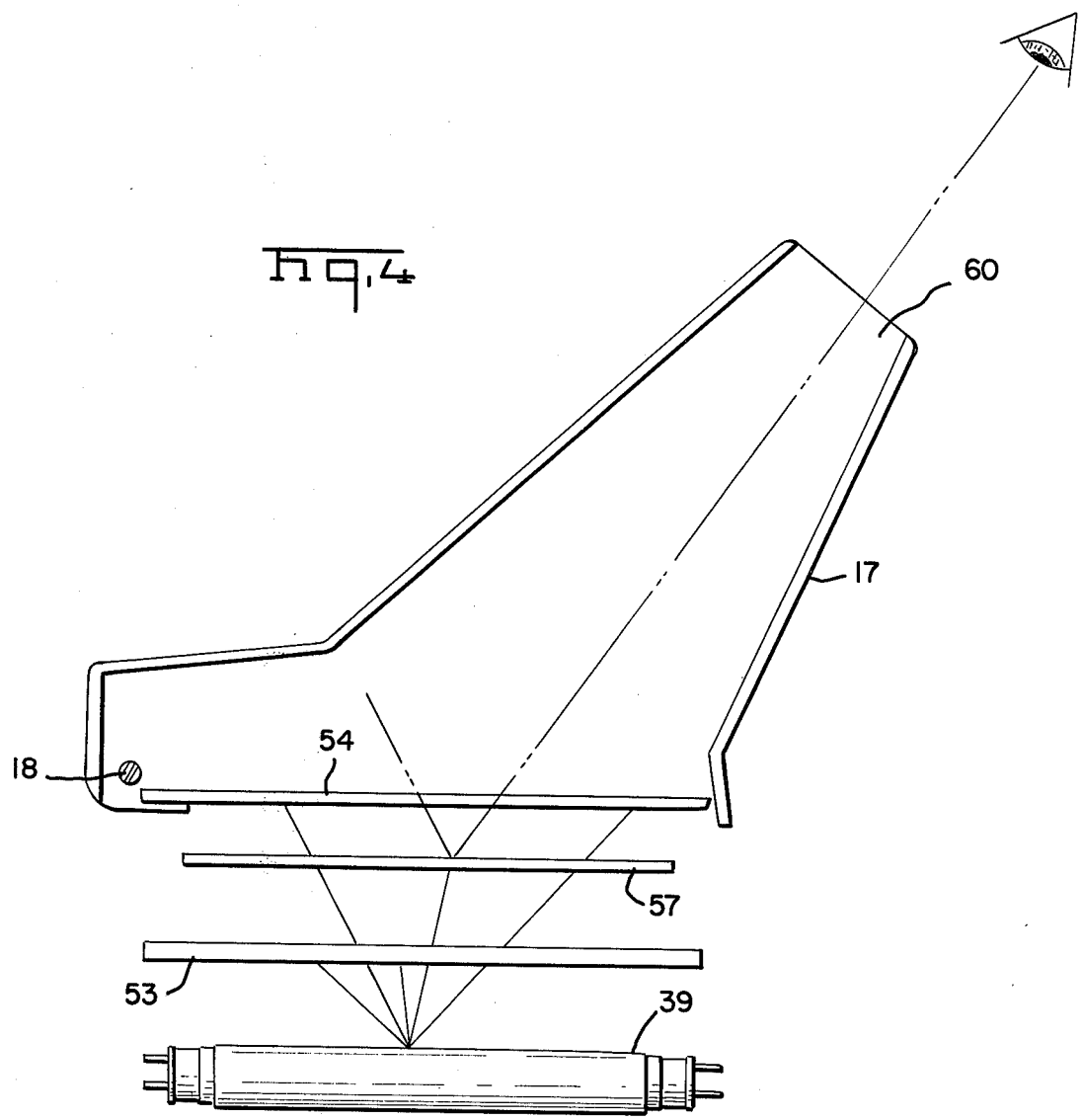
FIG. 4 shows the integral viewer.
Figure 5:
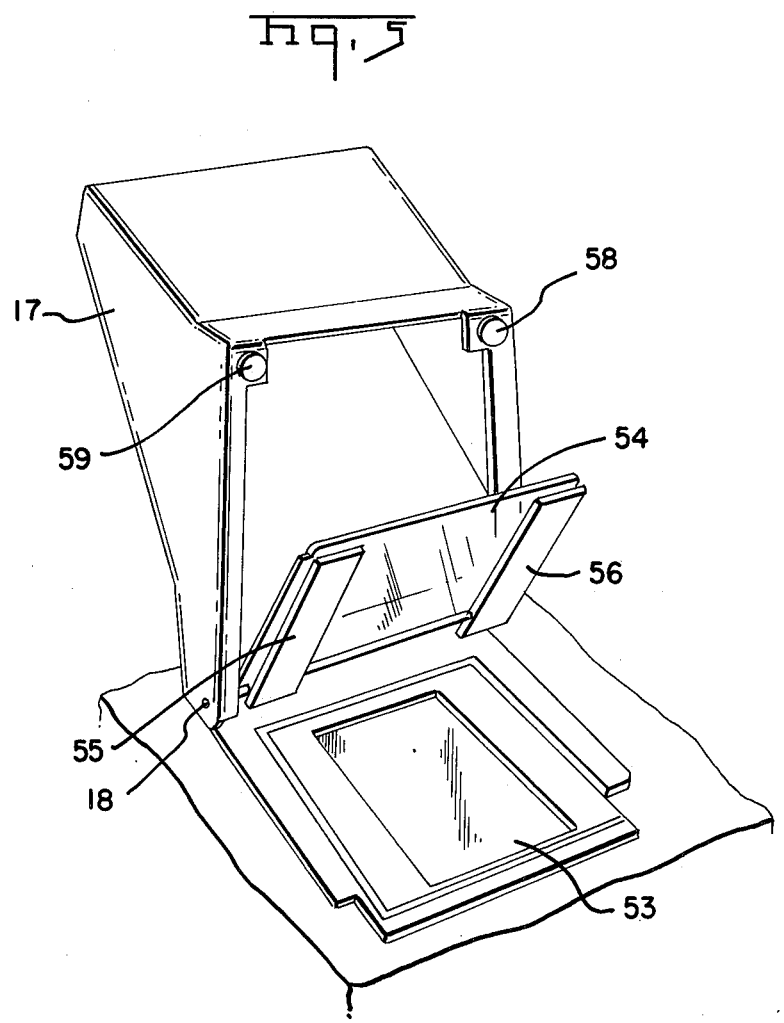
FIG. 5 shows the viewing sample holder and ultraviolet blocking filter.

FIGS. 4 and 5 show the integral viewer in more detail.

An ultraviolet pass filter 53 is mounted in the opening on top of the case. An ultraviolet blocking filter 54 is hingedly mounted in the bottom of shroud 17. As shown in FIG. 5, the shroud 17 is tilted back and the blocking filter 54 is raised on its hinge so that the film sample 57 can be placed over the pass filter 53. Hold down strips 55 and 56 cooperate with the edges of the pass filter 53 to form a viewing sample holder.

With the shroud tilted back, a camera rests on the ultraviolet blocking filter 54. This enables the operator to take pictures of the samples he has viewed.

An opening 60 (FIG. 4) is used to view the fluorescing sample. The shroud of viewer 17 almost totally excludes ambient room light from the area of the fluorescing sample 57 which is subject to uniform ultraviolet illumination from the lamp 39. The same lamps are used for viewing as for recording. The operator is shielded from ultraviolet light by the instrument case and by the ultraviolet blocking filter 54 in the bottom of the viewer. The viewer of this invention is a marked improvement over the prior art in that illumination of the sample is from underneath. This is possible because of the selective transmission filters which prevent the light source from being visible to the operator. This integral viewer provides an operator work station for viewing and photographing samples which can then be automatically scanned and fluorometric or densitometric measurements can be recorded.

While a particular embodiment of the invention has been shown and described, various modifications will occur to those skilled in the art. The appended claims are, therefore, intended to cover all such modifications which fall within the true spirit and scope of the invention.

What is claimed is:

1. An instrument for analyzing light fluorescing from samples excited by ultraviolet light comprising:
    a light detector responsive to light fluorescing from a sample and producing an output representing the intensity of said light,
    a recording device, the output of said detector being connected to said recording device for recording the intensity of light fluorescing from said sample,
    an integral viewer having a hood shielding a sample from ambient light and an opening for observation of light fluorescing from said sample, and
    an ultraviolet light source positioned so that ultraviolet light from the same source can excite a sample which fluoresces light incident upon said light detector and can excite a sample which fluoresces light observed through said viewer.

2. The instrument recited in claim 1 further comprising:
    a case, said viewer being hinged to said case, and
    a viewing sample holder including hold down strips between the bottom of said viewer and said case, said strips being disposed along sides of an opening in said case when said viewer is positioned over a sample placed upon said opening.

3. The instrument recited in claim 2 further comprising:
    an ultraviolet pass filter positioned in said opening.

4. The instrument recited in claim 2 further comprising:
    an ultraviolet blocking filter mounted in the bottom of said viewer so that it covers a sample positioned over the opening in said case, said ultraviolet blocking filter shielding the observer from ultraviolet light.

5. The instrument recited in claim 1 further comprising:
    a densitometric light source for irradiating said sample with light of a wavelength which is absorbed by a sample so that said recording device records densitometric measurements of said sample, and
    both said ultraviolet light source and said densitometric source being positioned on the opposite side of said sample from said recording device.

6. The instrument recited in claim 5 further comprising:
    an ultraviolet blocking filter positioned in the optical axis of said system between said sample and said recording device to discriminate against ultraviolet excitation of said recording device.

7. The instrument recited in claim 5 further comprising:
    a filter holder having an ultraviolet transmission filter and at least one filter for transmitting light from said densitometric source, said holder being selectively indexed to position one of said filters in the optical path between said light sources and said recording device.

8. An instrument for analyzing light fluorescing from samples excited by ultraviolet light comprising:
    a recording device for recording the intensity of light fluorescing from said sample, and
    a light source including two ultraviolet lamps positioned close to and on either side of the optical axis through said sample so that ultraviolet light from said lamps pass through said sample at an angle with said axis so that there is no direct ray path for ultraviolet light along said axis to said recording device, said light source exciting said sample which fluoresces light which travels along said axis to said recording device.

9. An instrument for analyzing light fluorescing from samples excited by ultraviolet light comprising:
    a recording device for recording the intensity of light fluorescing from a sample,
    an ultraviolet light source,
    a recording sample holder for positioning said sample between said light source and said recording device,
    an integral viewer having a hood shielding a sample from ambient light and an opening for observation of light fluorescing from said sample, a viewing sample holder for holding a sample between said light source and said integral viewer, said light source being positioned close to and on the opposite side of said recording sample holder from said light detector, said light source being positioned on the opposite side of said viewing sample holder from said viewer, ultraviolet light from said source exciting a sample in said recording sample holder which fluoresces light incident upon said recording device without blocking emanating light from said recording device, light from said source exciting a sample in said viewing sample holder which fluoresces light observed through said viewer without blocking emanating light from said viewer.

10. The instrument recited in claim 9 further comprising:

an ultraviolet pass filter between said source and said viewing sample holder for passing only ultraviolet light from said source to a sample.

11. The instrument recited in claim 10 further comprising:

a filter between said viewing sample holder and said viewer having a wavelength pass band which blocks ultraviolet light of said source and which passes light of the wavelength fluorescing from said sample so that the observer can see the fluorescing sample but is shielded from ultraviolet light.

12. An instrument for analyzing light from samples comprising:

a light detector responsive to light from a sample and producing an output representing the intensity of said light, a recording device, the output of said detector being connected to said recording device for recording the intensity of light from said sample, an integral viewer having a hood shielding a sample from ambient light and an opening for observation of light fluorescing from said sample, an ultraviolet light source positioned so that ultraviolet light from the same source can excite a sample which fluoresces light incident upon said light detector and can excite a sample which fluoresces light observed through said viewer, a densitometric light source for irradiating said sample with light of a wavelength which is adsorbed by a sample so that said recording device records densitometric measurements of said sample, both said ultraviolet light source and said densitometric source being positioned on the opposite side of said sample from said recording device, a filter holder having an ultraviolet transmission filter and at least one filter for transmitting light from said densitometric source, said holder being selectively indexed to position one of said filters in the optical path between said light sources and said recording device, and a mode selection switch actuated by said filter holder to energize said ultraviolet source when said ultraviolet transmission filter is in the optical path and to energize said densitometric source when a densitometric transmitting filter is in the optical path.

13. An instrument for analyzing light from samples comprising:

a light detector responsive to light from a sample and producing an output representing the intensity of said light, a recording device, the output of said detector being connected to said recording device for recording the intensity of light from said sample, an integral viewer having a hood shielding a sample from ambient light and an opening for observation of light fluorescing from said sample, an ultraviolet light source positioned so that ultraviolet light from the same source can excite a sample which fluoresces light incident upon said light detector and can excite a sample which fluoresces light observed through said viewer, a densitometric light source for irradiating said sample with light of a wavelength which is absorbed by a sample so that said recording device records densitometric measurements of said sample, both said ultraviolet light source and said densitometric source being positioned on the opposite side of said sample from said recording device, a filter holder having an ultraviolet transmission filter and at least one filter for transmitting light from said densitometric source, said holder being selectively indexed to position one of said filters in the optical path between said light sources and said recording device, a logarithmic amplifier for processing densitometric signals, and a mode switch actuated by said filter holder for connecting said logarithmic amplifier to said light detector when one of the densitometric filters is in the optical path of said instrument.

14. An instrument for making fluorometric and densitometric measurements of samples comprising:

a light detector producing an output representing the intensity of light from a sample, a recording device, the output of said light detector being connected to said recording device for recording the intensity of light from said sample, an ultraviolet source including two ultraviolet lamps positioned close to and on either side of the optical axis to a sample, said source being on the opposite side of said sample from said recording device, and a densitometric source positioned on the opposite side of said sample from said recording device, the optical path between said sample and said recording device being the same for both densitometric and fluorometric measurements.

15. The instrument recited in claim 14 further comprising:

an integral viewer, a recording sample holder for positioning said sample between said sources and said recording device, a viewing sample holder for holding said sample between said ultraviolet source and said integral viewer, said ultraviolet source being disposed close to and on the opposite side of the sample from said recording device and from said viewer to provide good excitation of a sample without blocking emanating light from said recording device or from said viewer.

16. The instrument recited in claim 14 further comprising:

an aperture stop in the optical path between said light source and said recording device to define the size and shape of the fluorescing image which is incident upon said recording device.

17. The instrument recited in claim 14 wherein said light detector is responsive to both fluorescing and densitometric light, and a logarithmic amplifier for processing densitometric signals so that the electrical signal produced is proportional to optical density or absorbence of said sample.

18. The instrument recited in claim 17 wherein said light detector is a solid state photo diode detector having a small sensitive area, and
an auxiliary imaging lens in said optical path for focusing light on said sensitive area.

19. The instrument recited in claim 14 further comprising:
a compound filter in the optical path between said sample and said recording device for passing only fluorescing light of a particular band of wavelengths to said recording device.

20. The instrument recited in claim 14 further comprising:
a filter holder having an ultraviolet transmission filter and at least one filter for transmitting light from said densitometric source, said holder being selectively indexed to position one of said filters in the optical path between said sources and said recording device.

21. An instrument for making fluorometric and densitometric measuements of samples comprising:
a recording device for recording the intensity of light from said sample,
an ultraviolet source positioned on the opposite side of said sample from said recording device,
a densitometric source positioned on the opposite side of said sample from said recording device,
a filter holder having an ultraviolet transmission filter and at least one filter for transmitting light from said densitometric source, said holder being selectively indexed to position one of said filters in the optical path between said sources and said recording device, and
a mode selection switch actuated by said filter holder to energize said ultraviolet source when said ultraviolet transmission filter is in the optical path and to energize said densitometric source when a densitometric transmission filter is in the optical path.

22. An instrument for making fluorometric and densitometric measurements of samples comprising:
a recording device for recording the intensity of light from said sample,
an ultraviolet source positioned on the opposite side of said sample from said recording device,
a densitometric source positioned on the opposite side of said sample from said recording device,
a filter holder having an ultraviolet transmission filter and at least one filter for transmitting light from said densitometric source, said holder being selectively indexed to position one of said filters in the optical path between said sources and said recording device,
a logarithmic amplifier for processing densitometric signals, and
a mode switch actuated by said filter holder for connecting said logarithmic amplifier to said recording device when one of the densitometric filters is in the optical path of said instrument.

* * * * *